United States Patent
Kerjean

(10) Patent No.: US 9,044,603 B2
(45) Date of Patent: Jun. 2, 2015

(54) PHOTO-GUIDING DEVICE FOR A RADIOTHERAPY APPARATUS

(76) Inventor: Joël Kerjean, Saint-Herblain (FR)

( * ) Notice: Subject to any disclaimer, the term of this patent is extended or adjusted under 35 U.S.C. 154(b) by 291 days.

(21) Appl. No.: 13/641,162

(22) PCT Filed: Apr. 1, 2011

(86) PCT No.: PCT/FR2011/050733
§ 371 (c)(1),
(2), (4) Date: Nov. 7, 2012

(87) PCT Pub. No.: WO2011/128550
PCT Pub. Date: Oct. 20, 2011

(65) Prior Publication Data
US 2013/0064350 A1    Mar. 14, 2013

(30) Foreign Application Priority Data
Apr. 15, 2010  (FR) .................................... 10 52870

(51) Int. Cl.
| | |
|---|---|
| *H05G 1/02* | (2006.01) |
| *G21K 1/00* | (2006.01) |
| *G02B 5/08* | (2006.01) |
| *G02B 7/182* | (2006.01) |
| *A61N 5/10* | (2006.01) |
| *A61B 6/06* | (2006.01) |
| *G21K 1/02* | (2006.01) |
| *G21K 1/06* | (2006.01) |
| *G02B 5/00* | (2006.01) |
| *F21V 8/00* | (2006.01) |

(52) U.S. Cl.
CPC .............. *A61N 5/1042* (2013.01); *G02B 5/005* (2013.01); *A61B 6/06* (2013.01); *G02B 6/0096* (2013.01); *A61N 2005/1091* (2013.01); *G21K 1/02* (2013.01); *G21K 1/067* (2013.01); *G21K 1/025* (2013.01)

(58) Field of Classification Search
CPC ............ A61B 6/06; G02B 5/00; G02B 5/005; G02B 6/06; G02B 6/0096; G02B 2006/0098; G21K 1/02
USPC ........... 378/65, 140, 145, 147, 149, 204, 210; 359/641, 838, 839, 850–853, 855, 867, 359/871, 894, 896
See application file for complete search history.

(56) References Cited

U.S. PATENT DOCUMENTS 2,638,554 A    5/1953  Bartow et al.
3,997,794 A *  12/1976  York et al. .................... 378/149

(Continued)

FOREIGN PATENT DOCUMENTS

| EP | 2071583 | 6/2009 |
| FR | 1 561 351 | 3/1969 |
| FR | 2706132 | 12/1994 |

OTHER PUBLICATIONS

International Search Report dated Aug. 5, 2011, corresponding to PCT/FR2011/050733.

*Primary Examiner* — Anastasia Midkiff
(74) *Attorney, Agent, or Firm* — Young & Thompson

(57) ABSTRACT

A photon-guiding device for a radiotherapy apparatus, consists of a central frustum, made up of a plurality of metal channels, and an outer casing that encloses the central frustum and consists of microchannels. The channels and microchannels have a frusto-conical shape and a common apex.

6 Claims, 1 Drawing Sheet

(56) References Cited

U.S. PATENT DOCUMENTS

| | | |
|---|---|---|
| 5,627,870 A | 5/1997 | Kopecky |
| 5,745,547 A * | 4/1998 | Xiao ............................. 378/145 |
| 6,624,431 B1 * | 9/2003 | Foster et al. ............... 250/505.1 |
| 6,749,300 B2 | 6/2004 | Bjeoumikhov |
| 7,471,866 B2 * | 12/2008 | Dumais et al. ................ 385/132 |
| 8,372,470 B2 * | 2/2013 | Hart et al. ......................... 427/8 |
| 2003/0209677 A1 | 11/2003 | Kumakhov |
| 2009/0279670 A1 * | 11/2009 | Verman et al. ................ 378/145 |
| 2010/0061511 A1 | 3/2010 | Heid |
| 2010/0296629 A1 | 11/2010 | Dabagov |

* cited by examiner

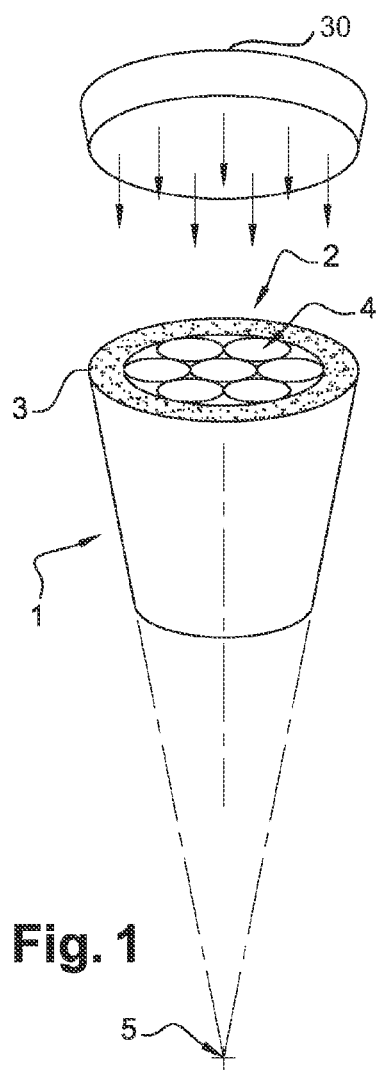
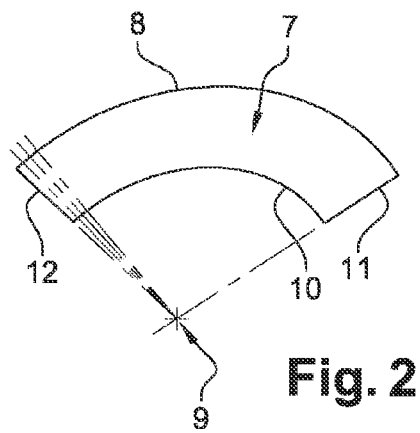
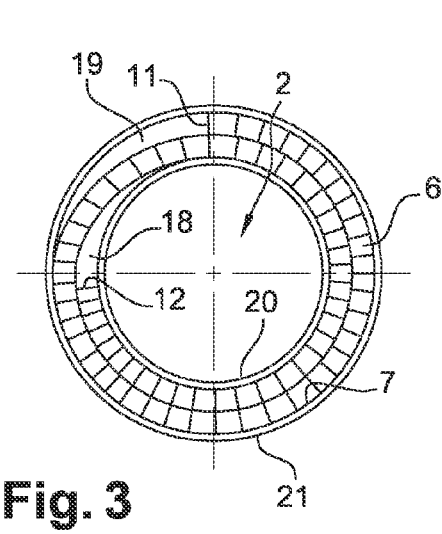
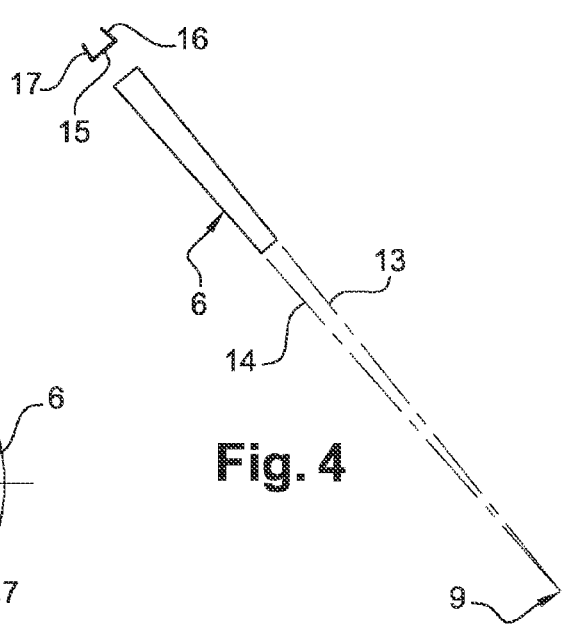
Fig. 1
Fig. 2
Fig. 3
Fig. 4

PHOTO-GUIDING DEVICE FOR A RADIOTHERAPY APPARATUS

The invention relates to a photon-guiding device for a radiotherapy apparatus.

A radiotherapy apparatus for treating cancerous tumors works by irradiating the tumors by means of high-energy photons, emitted by a natural or artificial source. These apparatuses are generally very heavy, and used in enclosed and shielded chambers for the protection of the staff, which makes communication between the patient and the doctor during the treatment sessions difficult.

Moreover, the criteria of effectiveness of the radiotherapy apparatuses are assessed according to two well defined biological effects:
- a lethal effect, obtained by concentration of photon beams ensuring a determined dose within a target volume,
- a so-called differential effect, obtained by the scattering of photon beams in a larger volume than the target, ensuring a lower dose, to allow healthy cells to regenerate.

The document U.S. Pat. No. 2,638,554 describes a photon-guiding device for a radiotherapy apparatus, consisting of a body in the form of a truncated cone, passed through by cylindrical channels which all converge at the apex of the cone. This document makes no mention of the differential effect.

One of the aims of the invention is to propose a photon-guiding device for a radiotherapy apparatus which makes it possible to combine both lethal and differential effects.

Another aim of the invention is to propose a photon-guiding device for a radiotherapy apparatus which is sufficiently simple and light to allow for the use of low-energy radiation sources.

The subject of the invention is a photon-guiding device for a radiotherapy apparatus, characterized in that it consists of a central truncated cone made up of a number of metal channels, and an outer body surrounding the central truncated cone and made up of micro channels, said channels and micro channels having a tapered form and a common apex.

Advantageously, said metal channels fill the volume of the central truncated cone by compact stacking.

According to one characteristic, the outer body is produced by spirally winding a metal sheet on which the micro channels are arranged.

Advantageously, the metal sheet is made up of a strip with circular curvature, contained between two concentric circular arcs and two lateral edges defined by two radii deriving from the same center.

According to one embodiment, each micro channel is in the form of a gutter with a bottom applied to the metal sheet and two slightly convergent flanks.

Advantageously, the spiral winding of the metal sheet is done on a support consisting of a first thin truncated cone having the outer dimensions of the central truncated cone.

The spiral winding of the metal sheet is done with the open side of the micro channels turned toward the first thin truncated cone.

Advantageously, for its spiral winding, the metal sheet is edged by two solid menisci, made of heavy metal.

By way of example, the invention is described hereinbelow with reference to the appended drawing in which:

FIG. 1 is a perspective view of an exemplary embodiment of a photon-guiding device according to the invention, FIG. 2 is a view of the cut metal sheet used as support for producing the photon-guiding device of FIG. 1, FIG. 3 is a plan view of the device of FIG. 1 showing the winding of the sheet of FIG. 2, FIG. 4 is an enlarged plan view of a micro channel with cross-sectional view.

Referring to the figures, the photon-guiding device 1 is of substantially tapered form, and consists of a central truncated cone 2 and a hollow tapered outer body 3.

The central truncated cone 2 is made up of a number of juxtaposed, tapered metal channels 4 having a common apex 5. These channels 4 fill the volume of the central truncated cone 2 by compact stacking.

The outer body 3 is made up of a set of micro channels 6 having the same common apex 5 as the channels 4 of the central truncated cone 2. These micro channels 6 are produced individually and fixed, by bonding for example, to a flat-cut metal sheet 7 (FIG. 2), the edges of which consist on the one hand of two concentric circular arcs and on the other hand of two radius portions. The two concentric circular arcs are: one, the outer arc 8, of radius R, plotted from the center 9; the other, the inner arc 10 of radius r less than R, plotted from the same center 9. The length of the other two edges, or lateral edges of the metal sheet 7, is the difference (R−r) between the two radii R and r. These two edges 11 and 12 are defined by two radii deriving from the same center 9. They correspond to the width of the sheet 7 which takes the form of a planar strip with circular curvature.

Each micro channel 6 is arranged on the planar metal sheet 7, and it occupies on the sheet the surface contained between two adjacent radii 13, 14 passing through the center 9. Each micro channel 6 is in the form of a gutter, with a bottom 15 and two flanks 16, 17. The bottom 15 is flat and applied to the sheet 7. The length of the bottom 15 is equal to the width of the sheet 7, i.e. (R−r).

The longitudinal edges of the bottom 15 are defined by two radii deriving from the center 9. Because of this, the width of the bottom 15 decreases between the outer edge 8 and the inner edge 10 of the sheet 7. The flanks 16 and 17 of each micro channel 6 rise up from the longitudinal edges of the bottom. Their height is limited by two radii deriving from the center 9, and is of the same order of magnitude as the width of the bottom 15.

The two flanks 16, 17 of a micro channel 6 are not parallel to one another but slightly convergent in light of the subsequent winding described below.

The micro channels 6 are juxtaposed on the sheet 7, their bottoms being adjacent and covering the surface of the sheet 7. The neighboring flanks of two adjacent micro channels 6 are slightly divergent on the still-flat sheet 7.

To produce the outer body 3, two thin truncated cones 20, 21, made of stainless steel, having the same apex 5, are used as supports. The first thin truncated cone 20 has substantially the outer dimensions of the central truncated cone 2. The second thin truncated cone 21 has the outer dimensions of the outer body 3.

On the first thin truncated cone 20, the following are wound in succession: a first solid meniscus 18 made of heavy metal such as lead or gold, the sheet 7 with the micro channels 6 with their open side turned toward the first thin truncated cone 20, and a second meniscus 19 of the same nature as the first. The sheet 7 provided with the micro channels 6 and the two menisci 18, 19 edging the sheet 7 constitute deformable and adjoining components in the outer body 3.

During this spiral winding, the neighboring flanks of two adjacent micro channels 6 are brought together and come into mutual contact. Once the winding is finished, the assembly is placed in the second thin truncated cone 21.

The central truncated cone 2 is put in place in the outer body 3 to complete the construction of the photon-guiding device.

In the duly constructed photon-guiding device, the metal channels 4 of the central truncated cone 2 and the micro channels 6 of the outer body 3 have a tapered form and a common apex 5.

The photon-guiding device is used in a radiotherapy apparatus to irradiate a target placed at the apex 5 (FIG. 1).

In this case, a radioactive source 30 is placed outside the photon-guiding device 1, on the surface of the large base of the truncated cone.

The large surface available makes it possible to use a source with a radioactive isotope of average specific activity, but great overall intensity.

The channels 4 of the central truncated cone 2 guide the photons which ensure the differential effect. These channels 4 use standard filtering and wide collimation technical means. The micro channels 6 of the outer body 3 guide, with great accuracy, the photons which ensure the lethal effect. The arrangement of the central truncated cone 2 and of the outer body 3, with different structures for the channels 4 and the micro channels 6, makes it possible to simultaneously ensure the irradiation with differential effect and the irradiation with lethal effect.

The arrangement of the micro channels 6 allows for the passage of the photons which are in the axis of the micro channels while stopping the others, which avoids the risk of a collateral carcinogenic effect.

The photon-guiding device has been described with a general truncated cone form. However, when the outer body 3 is of a certain thickness, the general form is more that of a portion of a sphere, the large outer surface being convex spherical and the small inner surface being concave spherical, the channels and micro channels converging at the single center of the two spherical surfaces.

As an example, for photon energies of 100 to 500 keV, the metal sheet has a thickness of 0.3 mm, the radius R is 14 cm, the radius r is 9 cm, the width of the sheet, or the height of the guiding device, is 5 cm, and the micro channels have an inner dimension of the order of 1.5 mm. Preferably, the photon-guiding device is made of gold.

In the case of an application of the photon-guiding device to a radiotherapy apparatus used for breast cancer, where the depth of penetration of the photons is very small, a radio isotope with low energy emission is suited to most cases: it is thulium 170, which has an emission similar to those used in mammography. In this case, the size of the photon-guiding device is very small and allows for an irradiation ballistic by circulation around the breast, which avoids the appearance of the so-called second, or induced breast cancer.

The invention claimed is:

1. A photon-guiding device for a radiotherapy apparatus comprising a central truncated cone made up of a number of metal channels filling the volume of the central truncated cone by compact stacking, and an outer body surrounding the central truncated cone and made up of micro channels, said metal channels and said micro channels having a tapered form and a common apex,
   wherein the outer body is produced by spirally winding a metal sheet on which the micro channels are arranged, and
   wherein each of said micro channels is in the form of a gutter with a bottom applied to the metal sheet and two slightly convergent flanks.

2. The photon-guiding device as claimed in claim 1, wherein the metal sheet is a strip with circular curvature contained between two concentric circular arcs and two lateral edges defined by two radii deriving from the same center.

3. The photon-guiding device as claimed in claim 1, wherein the micro channels are juxtaposed on the metal sheet.

4. A photon-guiding device for a radiotherapy apparatus comprising a central truncated cone made up of a number of metal channels filling the volume of the central truncated cone by compact stacking, and an outer body surrounding the central truncated cone and made up of micro channels, said metal channels and said micro channels having a tapered form and a common apex,
   wherein the outer body is produced by spirally winding a metal sheet on which the micro channels are arranged, and
   wherein the metal sheet comprises a first thin truncated cone defining outer dimensions of the central truncated cone.

5. The photon-guiding device as claimed in claim 4, wherein the micro channels have an open side facing said first thin truncated cone.

6. The photon-guiding device as claimed in claim 5, wherein the metal sheet is edged by two solid menisci made of heavy metal.

\* \* \* \* \*